(12) United States Patent
Suzuki et al.

(10) Patent No.: US 6,764,545 B2
(45) Date of Patent: Jul. 20, 2004

(54) PRODUCTION METHOD OF EPOXIDE CRYSTAL

(75) Inventors: Yuichi Suzuki, Kawasaki (JP); Naoko Hirose, Kawasaki (JP); Tomoyuki Onishi, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 52 days.

(21) Appl. No.: 10/011,304

(22) Filed: Dec. 11, 2001

(65) Prior Publication Data

US 2002/0087014 A1 Jul. 4, 2002

(30) Foreign Application Priority Data

Dec. 12, 2000 (JP) ........................................ 2000-377804
Feb. 26, 2001 (JP) ........................................ 2001-051108

(51) Int. Cl.$^7$ ................................................ C30B 7/08
(52) U.S. Cl. ........................ 117/68; 117/925; 117/927; 549/521; 549/529; 549/530
(58) Field of Search .................. 549/521, 529, 549/530; 117/68, 927, 925

(56) References Cited

U.S. PATENT DOCUMENTS 3,620,983 A * 11/1971 Porret
3,676,433 A * 7/1972 Parikh
5,166,371 A * 11/1992 Shum et al. ................. 549/529
5,481,011 A 1/1996 Chen et al.
5,936,104 A * 8/1999 Nishiyama et al. ......... 549/521

FOREIGN PATENT DOCUMENTS

| EP | 0 580 402 | 1/1994 |
|---|---|---|
| EP | 0 754 669 | 1/1997 |
| EP | 1 052 257 | 11/2000 |
| EP | 1 067 125 | 1/2001 |
| EP | 1 081 133 | 3/2001 |
| JP | 6-206857 | 7/1994 |
| WO | WO 99/38855 | 8/1999 |
| WO | WO 00/44736 | 8/2000 |

OTHER PUBLICATIONS

A. A. Malik. The 3$^{rd}$ International Conference on Organic Process Research & Development, pps. 1–16, "Development of a Commercial Process for 2S. 3S and 2R. 3S–Epoxides", Jul. 10–12, 2000.

T. Archibald, et al., Scientific Update Conference Manual, Chiral USA '99, pps. 1–10, "Full Scale Chiral Separations Using SMB" and "Aerojet Fine Chemicals", pps. 1–4, May 4, 1999.

J. C. Barrish, et al., Journal of Medicinal Chemistry, vol. 37, No. 12, XP–001002509, pp. 1758–1768, "Aminodiol HIV Protease Inhibitors. 1. Design, Synthesis, and Preliminary SAR", 1994.

* cited by examiner

*Primary Examiner*—Robert Kunemund
(74) *Attorney, Agent, or Firm*—Oblon, Spivak, McClelland, Maier & Neustadt, P.C.

(57) ABSTRACT

The present invention provides a production method including adding water to a solution of (2R,3S)-3-tert-butoxycarbonylamino-1,2-epoxy-4-phenylbutane ((2R,3S)-epoxide compound) or (2S,3R)-3-tert-butoxycarbonylamino-1,2-epoxy-4-phenylbutane ((2S,3R)-epoxide compound) in a polar solvent to allow crystallization, whereby to produce crystals of the (2R,3S)-epoxide compound or the (2S,3R)-epoxide compound conveniently in a high yield by an industrial production method without requiring an extremely low temperature.

20 Claims, No Drawings

PRODUCTION METHOD OF EPOXIDE CRYSTAL

TECHNICAL FIELD OF THE INVENTION

The present invention relates to a production method of a crystal of (2R,3S)-3-tert-butoxycarbonylamino-1,2-epoxy-4-phenylbutane and a crystal of (2S,3R)-3-tert-butoxycarbonylamino-1,2-epoxy-4-phenylbutane.

BACKGROUND OF THE INVENTION

The (2R,3S)-3-tert-butoxycarbonylamino-1,2-epoxy-4-phenylbutane [the following formula (1), hereinafter sometimes to be referred to as a (2R,3S)-epoxide compound] and (2S,3R)-3-tert-butoxycarbonylamino-1,2-epoxy-4-phenylbutane [the following formula (2), hereinafter sometimes to be referred to as a (2S,3R)-epoxide compound] are useful as intermediates for pharmaceutical compounds such as HIV protease inhibitor and the like [see, for example, A. A. Malik, The 3rd International Conference on Organic Process Research & Development, Development of a Commercial Process for 2S,3S and 2R,3S-epoxides, Jul. 10–12, 2000, Montreal, T. Archibald et al., Scientific Update Conference Manual, Chiral USA '99, Full Scale Chiral Separations Using SMB, May 4, 1999, San Francisco, Scientific Update].

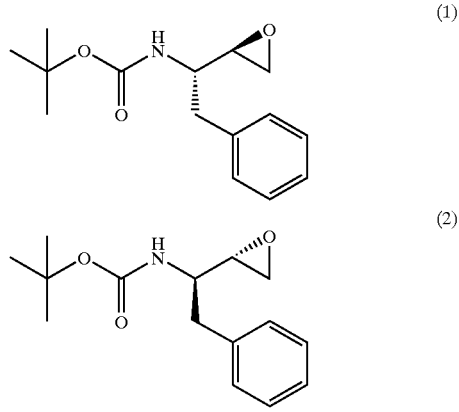

The (2R,3S)-epoxide compound and (2S,3R)-epoxide compound are relatively difficult to crystallize and the development of a method of producing the crystals of these compounds at an industrial scale has been desired. While the production methods of these compounds are disclosed in JP-A-6-206857 (EP0580402), WO99/38855, WO00/44736 and the like, they are not necessarily sufficient as a method for industrially producing the crystals.

For example, JP-A-6-206857 (EP0580402) discloses a method comprising treating (2R,3S)-3-tert-butoxycarbonylamino-1-chloro-2-hydroxy-4-phenylbutane with an aqueous KOH solution in ethanol to give (2R,3S)-epoxide compound, removing alkali and the like by extraction, dissolving the compound by refluxing in ethyl acetate and adding hexane to the obtained solution for crystallization. WO99/38855 discloses a method comprising reacting (2R,3S)-3-tert-butoxycarbonylamino-2-hydroxy-4-phenyl-1-butanol with alkylsulfonyl halide compound or arylsulfonyl halide compound in an organic solvent in the presence of a base for sulfonation to give (2R,3S)-3-tert-butoxycarbonylamino-2-hydroxy-4-phenyl-1-methanesulfonyloxybutane, treating the compound with a base and crystallizing the obtained (2R,3S)-epoxide compound from an aliphatic hydrocarbon solvent such as hexane and the like.

According to the above-mentioned methods, however, a complicated step of extraction and the like is necessary to remove alkali and the like remaining in the system after production of the (2R,3S)-epoxide compound. In addition, a poor solvent used (e.g., hexane etc.) dissolves the objective product of the present invention to some extent, and the crystallization ratio tends to decrease. Therefore, crystallization should be conducted at an extremely low temperature of −20° C. (WO99/38855) or −40° C. (JP-A-6-206857) to increase the ratio. As such, these methods are not necessarily sufficient for industrial production.

WO00/44736 discloses a crystallization method comprising treating (2R,3S)-3-tert-butoxycarbonylamino-1-chloro-2-hydroxy-4-phenylbutane with aqueous sodium hydroxide solution in acetone to give (2R,3S)-epoxide compound, separating the aqueous phase, dissolving the obtained (2R,3S)-epoxide compound in a mixed solvent of acetone and water and adding the resulting solution to water. According to this method, however, a solution of the objective product is added dropwise to a poor solvent to allow rapid crystallization. As a result, crystals may aggregate or form scales and the like depending on the conditions of the dropwise addition, stirring and the like. In addition, a solution of the objective product needs to be added into a different container containing the poor solvent, which makes the method not entirely suitable for an industrial production.

SUMMARY OF THE INVENTION

The present invention aims at providing a method for industrial scale production of a crystal of (2R,3S)-3-tert-butoxycarbonylamino-1-epoxy-4-phenylbutane and a crystal of (2S,3R)-3-tert-butoxycarbonylamino-1,2-epoxy-4-phenylbutane, which method is free of the above-mentioned problems (e.g., complicated operation, extremely low temperature necessary for crystallization and the like).

According to the present invention, water is added to a solution of (2R,3S)-3-tert-butoxycarbonylamino-1,2-epoxy-4-phenylbutane or an optical isomer thereof, (2S,3R)-3-tert-butoxycarbonylamino-1,2-epoxy-4-phenylbutane, in a polar solvent, to allow crystallization, whereby crystals superior in filtration property and separation property are obtained conveniently in a high yield without requiring an extremely low temperature.

Accordingly, the present invention provides the following.

[1] A method for producing a crystal of (2R,3S)-3-tert-butoxycarbonylamino-1,2-epoxy-4-phenylbutane ((2R,3S)-epoxide compound) of the above-mentioned formula (1) or (2S,3R)-3-tert-butoxycarbonylamino-1,2-epoxy-4-phenylbutane ((2S,3R)-epoxide compound) of the above-mentioned formula (2), which method comprises adding water to a solution of the (2R,3S)-epoxide compound or the (2S,3R)-epoxide compound in a polar solvent to allow crystallization.

[2] The method of the above-mentioned [1], wherein the crystallization comprises a step of starting precipitation of crystals and aging the crystals precipitated.

[3] The method of the above-mentioned [1], wherein the crystallization is conducted at a temperature of not higher than 16° C.

[4] The method of the above-mentioned [1], wherein the polar solvent is one or more kinds of solvent(s) selected from group (A) consisting of methanol, ethanol, 1-propanol and 2-propanol, or a mixed solvent of water and one or more kinds of solvent(s) selected from the group (A).

[5] The method of the above-mentioned [1], wherein the polar solvent is 2-propanol or a mixed solvent of water and 2-propanol.

[6] A method for producing a crystal of (2R,3S)-3-tert-butoxycarbonylamino-1,2-epoxy-4-phenylbutane or (2S,3R)-3-tert-butoxycarbonylamino-1,2-epoxy-4-phenylbutane, which method comprises treating (2R,3S)-3-tert-butoxycarbonylamino-1-halo-2-hydroxy-4-phenylbutane of the following formula (3)

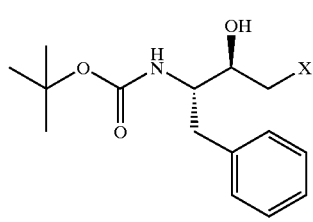

(3)

wherein X is a halogen atom, or (2S,3R)-3-tert-butoxycarbonylamino-1-halo-2-hydroxy-4-phenylbutane of the following formula (4)

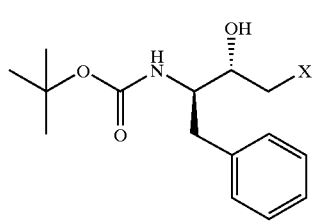

(4)

wherein X is a halogen atom, with a base in a polar solvent to give a solution of (2R,3S)-epoxide compound or (2S,3R)-epoxide compound in a polar solvent, and adding water to the obtained solution to allow crystallization.

[7] The method of the above-mentioned [6], wherein X is a chlorine atom.

[8] The method of the above-mentioned [6], wherein the crystallization comprises a step of starting precipitation of crystals and aging the crystals precipitated.

[9] The method of the above-mentioned [6], wherein the crystallization is conducted at a temperature of not higher than 16° C.

[10] The method of the above-mentioned [6], wherein the polar solvent is one or more kinds of solvent(s) selected from group (A) consisting of methanol, ethanol, 1-propanol and 2-propanol, or a mixed solvent of water and one or more kinds of solvent(s) selected from the group (A).

[11] The method of the above-mentioned [6], wherein the polar solvent is 2-propanol or a mixed solvent of water and 2-propanol.

[12] A method for producing a crystal of (2R,3S)-3-tert-butoxycarbonylamino-1,2-epoxy-4-phenylbutane or (2S,3R)-3-tert-butoxycarbonylamino-1,2-epoxy-4-phenylbutane, which method comprises treating (2R,3S)-3-tert-butoxycarbonylamino-1-chloro-2-hydroxy-4-phenylbutane or (2S,3R)-3-tert-butoxycarbonylamino-1-chloro-2-hydroxy-4-phenylbutane with a base in a polar solvent to give a solution of (2R,3S)-epoxide compound or (2S,3R)-epoxide compound in a polar solvent, and adding water to the obtained solution to allow crystallization.

[13] The method of the above-mentioned [12], wherein the crystallization comprises a step of starting precipitation of crystals and aging the crystals precipitated.

[14] The method of the above-mentioned [12], wherein the crystallization is conducted at a temperature of not higher than 16° C.

[15] The method of the above-mentioned [12], wherein the polar solvent is one or more kinds of solvent(s) selected from group (A) consisting of methanol, ethanol, 1-propanol and 2-propanol, or a mixed solvent of water and one or more kinds of solvent(s) selected from the group (A).

[16] The method of the above-mentioned [12], wherein the polar solvent is 2-propanol or a mixed solvent of water and 2-propanol.

DETAILED DESCRIPTION OF THE INVENTION

The present invention is described in detail in the following. In the present specification, (2R,3S)-epoxide compound and/or (2S,3R)-epoxide compound may be sometimes referred to as "the objective product".

Production methods of (2R,3S)-epoxide compound and (2S,3R)-epoxide compound

The (2R,3S)-epoxide compound is a known compound, which can be produced by, for example, treating (2R,3S)-3-tert-butoxycarbonylamino-1-halo-2-hydroxy-4-phenylbutane of the following formula (3)

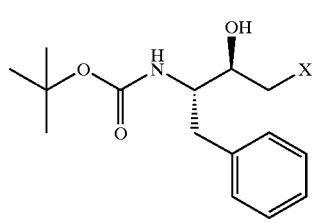

(3)

wherein X is a halogen atom, with a base. Similarly, the (2S,3R)-epoxide compound can be produced by, for example, treating (2S,3R)-3-tert-butoxycarbonylamino-1-halo-2-hydroxy-4-phenylbutane of the following formula (4)

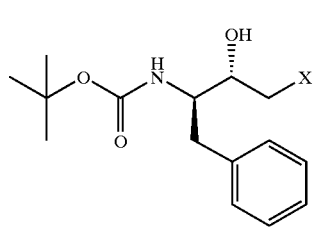

(4)

wherein X is a halogen atom, with a base [see, for example, JP-A-6-206857 (EP0580402) etc.].

As the halogen atom at X, chlorine atom and bromine atom are preferable, and particularly chlorine atom is preferable.

The base to be used for the production of (2R,3S)-epoxide compound and (2S,3R)-epoxide compound is not particularly limited, but preferred are, for example, potassium hydroxide, sodium hydroxide, potassium carbonate, sodium carbonate, sodium methoxide, sodium ethoxide and potassium tert-butoxide.

As the polar solvent to be used for the production of (2R,3S)-epoxide compound and (2S,3R)-epoxide compound, those used for the crystallization step to be mentioned below are exemplified.

The above-mentioned (2R,3S)-3-tert-butoxycarbonylamino-1-halo-2-hydroxy-4-phenylbutane is also a known compound, which can be produced by, for example, reducing (3S)-3-tert-butoxycarbonylamino-1- halo-4-phenyl-2-butanone. Similarly, (2S,3R)-3-tert-butoxycarbonylamino-1-halo-2-hydroxy-4-phenylbutane can be produced by, for example, reducing (3R)-3-tert-butoxycarbonylamino-1-halo-4-phenyl-2-butanone [see, for example, P. Raddatz et al., J. Med. Chem., 34, 11, 3269 (1991), A. A. Malik, The 3rd International Conference on Organic Process Research & Development, Development of a Commercial Process for 2S,3S and 2R,3S-epoxides, Jul. 10–12, 2000, Montreal, or T. Archibald et al., Scientific Update Conference Manual, Chiral USA '99, Full Scale Chiral Separations Using SMB, May 4, 1999, San Francisco, Scientific Update].

Crystallization method of (2R,3S)-epoxide compound and (2S,3R)-epoxide compound

The crystallization method is explained in the following by referring to (2R,3S)-epoxide compound as an example. An optical isomer thereof, (2S,3R)-epoxide compound, can be also crystallized by a similar method.

First, (2R,3S)-epoxide compound is dissolved in a polar solvent. The polar solvent in the present invention is not particularly limited as long as it is a good solvent for the objective product and easily miscible with water. Examples of the polar solvent include organic solvent miscible with water (e.g., methanol, ethanol, 1-propanol, 2-propanol, acetone, 2-butanone, acetonitrile, tetrahydrofuran etc.), where one or more kinds of these may be used in combination, a mixed solvent of one or more kinds of these organic solvents and water, and the like. Preferable polar solvent may be, for example, alcohol such as methanol, ethanol, 1-propanol, 2-propanol and the like, and a mixed solvent of these alcohols and water, particularly preferably 2-propanol and a mixed solvent of water and 2-propanol. Water acts as a poor solvent for the objective product. A different solvent may be present as long as the effect of the present invention is not impaired.

When the above-mentioned mixed solvent of an organic solvent and water is used as a polar solvent, the mixing ratio varies depending on the content of the objective product, crystallization temperature and the like. A suitable ratio can be determined appropriately by those of ordinary skill in the art. Preferable volume ratio is water being not more than 10, more preferably not more than 5, relative to organic solvent being 1.

The concentration of the polar solvent solution containing the objective product, which is to be subjected to a crystallization step, is not particularly limited. Preferable conditions can be determined appropriately by those of ordinary skill in the art, in consideration of the kind of the polar solvent to be used, crystallization temperature and the like. Preferable concentration is not lower than 5 wt %.

When (2R,3S)-3-tert-butoxycarbonylamino-1-chloro-2-hydroxy-4-phenylbutane is treated with a base to give (2R,3S)-epoxide compound and the above-mentioned polar solvents are used as a reaction solvent, the reaction mixture can be used as it is or used directly for a crystallization step after appropriate concentration. In this way, the objective product can be produced more conveniently. In this case, the base and the like present in the reaction mixture do not need to be removed specifically but the reaction mixture is preferably subjected to crystallization after neutralization with an acid, such as hydrochloric acid, sulfuric acid, citric acid and the like.

According to the present invention, water is added to a solution of the objective product in a polar solvent to allow crystallization. Because water, which is a poor solvent, is added to the solution containing the objective product, the crystals can be precipitated under relatively mild conditions, and scaling is not produced easily.

On the other hand, in the case that the crystallization is performed, for example, by cooling in a mixture solvent of water and a polar solvent without adding water, the resulting slurry is inferior in fluidity and the obtained crystals are inferior in filtration property and separation property, so that it is not suitable for an industrial production.

The crystallization is preferably performed at a temperature of not higher than 16° C., at which the solvent does not solidify. For example, the crystallization is preferably performed at −10° C. to 16° C., particularly preferably 0° C. to 10° C. When crystallization is performed at a temperature exceeding 16° C., the objective product unpreferably tends to become oily.

To produce a crystal superior in filtration property and separation property and to suppress coagulation and scaling of crystals in the present invention, crystallization is preferably started and the precipitated crystals are aged before adding water.

The method for starting precipitation is not particularly limited, and, for example, (i) a method for adding water, (ii) a method for adding a seed crystal, (iii) a method for cooling the solution and the like are mentioned. These methods can be optionally combined. When, for example, the aforementioned (i) and (ii) are combined, the seed crystal can be added concurrently with water or thereafter.

The amount of water to be added in (i) may be an amount that starts precipitation of the crystals of the objective product. The temperature of water to be added in (i) is not particularly limited, but it is preferably about the same as the temperature of the crystallization.

The amount of addition of the seed crystal in (ii) can be determined as appropriate, which is generally preferably about 0.01%–3% relative to the objective product present in a solution.

The aging applied after starting the precipitation of the crystals is preferably performed under stirring and the temperature is preferably lowered from the temperature at the start of the crystal precipitation. The time of aging is not particularly limited, and is, for example, about 10 min–24 h, preferably about 30 min–2 h.

Water is added after the aging step. Water is preferably added while appropriately stirring the solution of the polar solvent, thereby not to easily cause coagulation or scaling of crystals and the like. Those of ordinary skill in the art can properly set the stirring conditions easily as long as such problems do not occur. Water can be added at a lower temperature than that for aging.

The amount of water to be added also varies depending on the conditions of concentration, crystallization temperature and the like of the objective product and is not particularly limited. It is generally about 50–500%, preferably about 100–300%, in volume ratio relative to the polar solvent when crystallization is started. The rate of adding water is not particularly limited, and water may be added gradually generally over 20 min to 4 h. The temperature of water to be added is not particularly limited, but preferably about the same as the crystallization temperature. Those of ordinary skill in the art can set the preferable amount and rate of addition of water and the like according to various conditions.

According to the production method of the present invention, when a high polarity impurity is contained, it is removed to the mother liquor side, whereby the objective product can be separated from the high polarity impurity. Therefore, the method of the present invention can be used as a purification method of the objective product, (2R,3S)-epoxide compound and (2S,3R)-epoxide compound.

When the objective product is obtained by the above-mentioned known method and the like, the objective product is subjected to the method of the present invention without isolation from the reaction mixture. As a result, alkali and salt contained in the reaction mixture are removed to the mother liquor side simultaneously with crystallization of the objective product. Consequently, the objective product obtained by a known method and the like can be easily isolated as a crystal without particularly requiring extraction and the like. As such, the present invention provides a superior production method. Moreover, when the same polar solvent as used for the crystallization step is used for the production of the objective product, the reaction mixture can be used directly for the crystallization step, thereby affording production of the objective product by a more convenient method.

The obtained crystal can be purified as necessary according to a conventional method, such as washing with a solvent, such as water, a mixed solvent of water and alcohol and the like, washing a slurry after adding water and the like, to provide a crystal having a higher purity.

According to the production method of the present invention, (2R,3S)-epoxide compound and (2S,3R)-epoxide compound, which cannot be obtained easily as a crystal, can be conveniently obtained, and the obtained crystals show uniform particle sizes and are superior in filtration property and separation property. Moreover, the method of the present invention produces crystals under relatively mild conditions, by the addition of a poor solvent to a solution containing the objective product. Therefore, control of the coagulation and scaling of the crystals is easy and the method is convenient. The resulting slurry is superior in fluidity, thereby preventing clogging of conduit and the like during delivery of the slurry from a crystallization can.

The method of the present invention does not require a special or excessive solvent or manipulation, facility and the like. Therefore, it is a superior production method that can be conveniently employed for industrial production.

EXAMPLES

The present invention is explained in detail in the following by way of Examples. It is needless to say that the present invention is not limited by these Examples.

Reference Example
Production of (2R,3S)-epoxide compound (2R,3S)-3-tert-Butoxycarbonylamino-1-chloro-2-hydroxy-4-phenylbutane (18.5 g) was cast in a 500 ml round-bottom flask and 2-propanol (101.05 ml) and water (33.75 ml) were added to allow dissolution. The mixture was cooled to 4° C. For stirring, a semicircular stirring plate (7.5 cm) was installed and the rate of rotation was set to 250 rpm. Aqueous NaOH solution (4 mol/L, 25.3 ml) was added to this solution and the mixture was stirred while maintaining the temperature at 4° C. for 60 min. By the above operation, a reaction solution containing (2R,3S)-epoxide compound (15.24 g) was obtained.

Example 1

While maintaining the reaction solution containing (2R,3S)-epoxide compound, which was obtained in the above-mentioned Reference Example, at 4° C., citric acid (2.16 g) and water (21.8 ml) were added to neutralize the reaction mixture. Water (20.2 ml) was further added and then a seed crystal (20 mg) was added and the start of precipitation was confirmed. After the start of the precipitation, the crystals were aged with stirring at 4° C. for 1 h. While maintaining the reaction mixture at 4° C., water (101 ml, 4° C.) was added dropwise thereto over 1 h with stirring.

The particle size distribution of the crystal in the obtained slurry was measured with FBRM, M-500L (Lasentec). As a result, the average particle size was 100 $\mu$m, indicating that the slurry was free of bulky aggregates, had uniform particle size distribution, superior fluidity and fine dischargeability.

This slurry was filtered through Kiriyama filter paper 5A. The slurry showed fine filtration property and separation property ((2R,3S)-epoxide compound in wet crystals: yield 15.0 g, yield 98.4%).

The obtained wet crystals were dried at 35° C. in vacuo until water content became not more than 0.1% to give crystals of (2R,3S)-epoxide compound.

Example 2

While maintaining the reaction solution containing (2R,3S)-epoxide compound, which was obtained in the above-mentioned Reference Example, at 4° C., citric acid (2.16 g) and water (21.8 ml) were added to neutralize the reaction mixture. Water (20.2 ml) was further added and then a seed crystal (20 mg) was added and the start of precipitation was confirmed. After the start of the precipitation, the crystals were aged with stirring at 4° C. for 1 h. While maintaining the reaction mixture at 4° C., water (101 ml, 4° C.) was added dropwise thereto over 1 h with stirring.

The particle size distribution of the crystal in the obtained slurry was measured with FBRM, M-500L (Lasentec). As a result, the average particle size was 100 $\mu$m, indicating that the slurry was free of bulky aggregates, had uniform particle size distribution, superior fluidity and fine dischargeability.

This slurry was filtered through Kiriyama filter paper 5A. The slurry showed fine filtration property and separation property.

To the obtained wet crystals was added water (202 ml) and the slurry was washed and filtrated. The obtained wet crystals were washed with water (202 ml) and dried at 35° C. in vacuo until water content became not more than 0.1% to give crystals of (2R,3S)-epoxide compound: yield 93.4% (14.23 g).

Example 3

(2R,3S)-3-tert-Butoxycarbonylamino-1-chloro-2-hydroxy-4-phenylbutane (5.50 g) was dissolved in a mixed solvent of 2-propanol (13.2 ml) and water (5.0 ml), and the solution was cooled to 4° C. 29% Aqueous sodium hydroxide solution (2.92 ml) was added and the mixture was stirred at 4° C. for 2.5 h. After the reaction was stopped by adding 27.7% aqueous citric acid solution (2.1 g), water (4.2 ml) was added dropwise over 10 min with stirring, thereby seeding was completed. Water (17.2 ml) was further added dropwise over generally about 30 min–4 h with stirring, and the mixture was stirred overnight at 4° C. to crystallize (2R,3S)-epoxide compound. The obtained slurry was filtered through Kiriyama filter paper 5A, washed with water (44 ml) and dried overnight at room temperature under reduced pressure to give the objective crystal of (2R,3S)-epoxide compound (4.76 g, yield 98.6%).

According to the present invention, the crystals of (2R,3S)-epoxide compound and (2S,3R)-epoxide compound superior in filtration property and separation property can be produced conveniently in a high yield by an industrial production method without requiring an extremely low temperature.

This application is based on patent application Nos. 2000-377804 and 2001-051108 filed in Japan, the contents of which are hereby incorporated by reference.

What is claimed is:

1. A method for producing a crystal of (2R,3S)-3-tert-butoxycarbonylamino-1,2-epoxy-4-phenylbutane of the following formula (1)

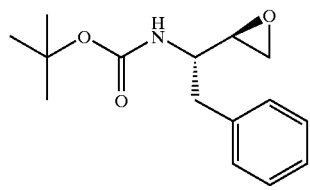

(1)

or (2S,3R)-3-tert-butoxycarbonylamino-1,2-epoxy-4-phenylbutane of the following formula (2)

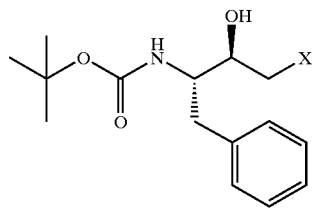

(2)

which method comprises (i) providing a solution of said (2R,3S)-3-tert-butoxycarbonylamino-1,2-epoxy-4-phenylbutane or said (2S,3R)-3-tert-butoxycarbonylamino-1,2-epoxy-4-phenylbutane in a polar solvent;

(ii) starting crystallization of said (2R, 3S)-3-tert-butoxycarbonylamino-1,2-epoxy-4-phenylbutane or said (2S,3R)-3-tert-butoxycarbonylamino-1,2-epoxy-4-phenylbutane from said solution, to precipitate crystals; and (iii) adding water to said solution of said (2R,3S)-3-tert-butoxycarbonylamino-1,2-epoxy-4-phenylbutane or said (2S,3R)-3-tert-butoxycarbonylamino-1,2-epoxy-4-phenylbutane, to achieve further crystallization of said (2R,3S)-3-tert-butoxycarbonylamino-1,2-epoxy-4-phenylbutane or said (2S,3R)-3-tert-butoxycarbonylamino-1,2-epoxy-4-phenylbutane from said solution.

2. The method of claim 1, which further comprises:

(ii') aging crystals precipitated in step (ii) prior to step (iii).

3. The method of claim 1, wherein said crystallization is conducted at a temperature of not higher than 16° C.

4. The method of claim 1, wherein said polar solvent is one or more solvent selected from the group consisting of methanol, ethanol, 1-propanol, 2-propanol, a mixed solvent of water and methanol, a mixed solvent of water and ethanol, a mixed solvent of water and 1-propanol, a mixed solvent of water and 2-propanol, and mixtures thereof.

5. The method of claim 1, wherein said polar solvent is 2-propanol or a mixed solvent of water and 2-propanol.

6. The method of claim 1, wherein said step (i) providing a solution of said (2R,3S)-3-tert-butoxycarbonylamino-1,2-epoxy-4-phenylbutane or said (2S,3R)-3-tert-butoxycarbonylamino-1,2-epoxy-4-phenylbutane in a polar solvent is carried out by:

(i') treating (2R,3S)-3-tert-butoxycarbonylamino-1-halo-2-hydroxy-4-phenylbutane of the following formula (3)

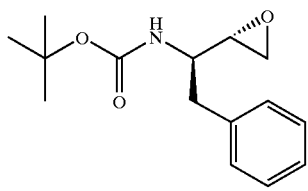

(3)

wherein X is a halogen atom, or (2S,3R)-3-tert-butoxycarbonylamino-1-halo-2-hydroxy-4-phenylbutane of the following formula (4)

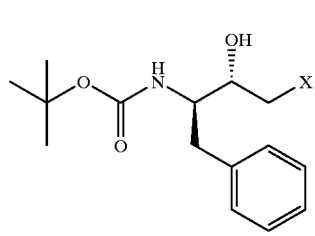

(4)

wherein X is a halogen atom, with a base in a polar solvent to give a solution of said (2R,3R)-3-tert-butoxycarbonylamino-1,2-epoxy-4-phenylbutane or said (2S,3R)-3-tert-butoxycarbonylamino-1,2-epoxy-4-phenylbutane in said polar solvent.

7. The method of claim 6, wherein X is a chlorine atom.

8. The method of claim 6, which further comprises:

(ii') aging crystals precipitated in step (ii) prior to step (iii).

9. The method of claim 6, wherein the crystallization is conducted at a temperature of not higher than 16° C.

10. The method of claim 6, wherein the polar solvent is one or more solvent selected from the group consisting of methanol, ethanol, 1-propanol, 2-propanol, a mixed solvent of water and methanol, a mixed solvent of water and ethanol, a mixed solvent of water and 1-propanol, a mixed solvent of water and 2-propanol, and mixtures thereof.

11. The method of claim 6, wherein said polar solvent is 2-propanol or a mixed solvent of water and 2-propanol.

12. The method of claim 6, wherein said base is at least one base selected from the group consisting of potassium hydroxide, sodium hydroxide, potassium carbonate, sodium carbonate, sodium methoxide, sodium ethoxide, potassium tert-butoxide, and mixtures thereof.

13. The method of claim 6, wherein said crystallization is carried out at a temperature of −10 to 16° C.

14. The method of claim 6, wherein said crystallization is carried out at a temperature of 0 to 10° C.

15. The method of claim 14, wherein said polar solvent is one or more solvent selected from the group consisting of methanol, ethanol, 1-propanol, 2-propanol, a mixed solvent of water and methanol, a mixed solvent of water and ethanol, a mixed solvent of water and 1-propanol, a mixed solvent of water and 2-propanol, and mixtures thereof.

16. The method of claim 14, wherein said polar solvent is 2-propanol or a mixed solvent of water and 2-propanol.

17. The method of claim 1, wherein said crystallization is carried out at a temperature of −10 to 16° C.

18. The method of claim 1, wherein said crystallization is carried out at a temperature of 0 to 10° C.

19. The method of claim 18, wherein said polar solvent is one or more solvent selected from the group consisting of methanol, ethanol, 1-propanol, 2-propanol, a mixed solvent of water and methanol, a mixed solvent of water and ethanol, a mixed solvent of water and 1-propanol, a mixed solvent of water and 2-propanol, and mixtures thereof.

20. The method of claim 18, wherein said polar solvent is 2-propanol or a mixed solvent of water and 2-propanol.

* * * * *